United States Patent [19]

Brunner

[11] Patent Number: 4,618,360
[45] Date of Patent: Oct. 21, 1986

[54] CYCLOHEXANEDIONECARBOXYLIC ACID DERIVATIVES WITH HERBICIDAL AND PLANT GROWTH REGULATING PROPERTIES

[75] Inventor: Hans-Georg Brunner, Lausen, Switzerland

[73] Assignee: Ciba-Geigy Corporation, Ardsley, N.Y.

[21] Appl. No.: 673,077

[22] Filed: Nov. 19, 1984

Related U.S. Application Data

[63] Continuation-in-part of Ser. No. 610,222, May 14, 1984.

[30] Foreign Application Priority Data

May 18, 1983 [CH] Switzerland .......................... 2693/83
Dec. 19, 1983 [CH] Switzerland .......................... 6747/83

[51] Int. Cl.⁴ ............... C07C 103/737; C07D 207/06; C07D 211/06; C07D 295/18; A01N 43/36; A01N 43/40; A01N 43/84; A01N 37/18
[52] U.S. Cl. ......................................... 71/88; 71/94; 71/95; 71/97; 71/98; 71/105; 71/106; 71/113; 71/118; 558/405; 544/158; 544/168; 544/173; 544/174; 546/226; 548/539; 556/117; 556/130; 556/146; 560/118; 560/125; 560/126; 562/500; 562/507; 562/508; 564/123; 564/188; 564/191
[58] Field of Search ................. 71/88, 94, 95, 98, 105, 71/106, 113, 118, 97; 260/465 D; 560/118, 125, 126; 564/188, 191, 123; 562/500, 507, 508; 544/168, 176, 158, 173, 174; 546/226; 548/539; 556/117, 130, 146

[56] References Cited

U.S. PATENT DOCUMENTS 3,950,420 4/1976 Sawaki et al. .......................... 560/125
3,989,737 11/1976 Sawaki et al. .......................... 560/125
4,422,864 12/1983 Becker et al. .......................... 71/88
4,440,566 4/1984 Luo .......................... 560/125
4,545,806 10/1985 Jahn et al. .......................... 71/88

FOREIGN PATENT DOCUMENTS 58-164543 9/1983 Japan.

Primary Examiner—Natalie Trousof
Assistant Examiner—Patricia M. Scott
Attorney, Agent, or Firm—Edward McC. Roberts; Kevin T. Mansfield

[57] ABSTRACT

Novel cyclohexanedionecarboxylic acid derivatives have herbicidal and plant growth regulating properties. The cyclohexanedionecarboxylic acid derivatives have the formula I

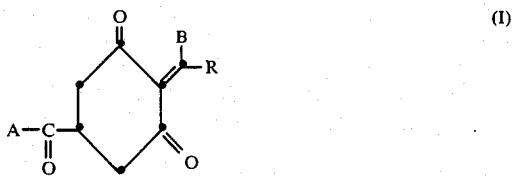

wherein
A is an —$OR_2$ or —$NR_3R_4$ radical,
B is hydroxyl, an —$NHOR_1$ radical or a metal or ammonium salt thereof
R is $C_1$-$C_6$alkyl or $C_3$-$C_6$cycloalkyl, each unsubstituted or substituted by halogen, $C_1$-$C_6$alkoxy or $C_2$-$C_4$alkythio,
$R_1$ is $C_1$-$C_6$alkyl, $C_1$-$C_6$haloalkyl, $C_3$-$C_6$alkenyl, $C_3$-$C_6$haloalkenyl or $C_3$-$C_6$alkynyl,
$R_2$, $R_3$ and $R_4$ are each independently hydrogen, $C_1$-$C_6$alkyl, $C_1$-$C_6$haloalkyl, $C_2$-$C_{10}$alkoxyalkyl, $C_2$-$C_{10}$alkylthioalkyl; $C_3$-$C_6$alkenyl which is unsubstituted or substituted by halogen, $C_1$-$C_4$alkoxy or $C_1$-$C_4$alkylthio; $C_3$-$C_6$alkynyl; phenyl or $C_1$-$C_6$aralkyl, wherein the phenyl nucleus is unsubstituted or substituted by halogen, $C_1$-$C_4$alkyl, $C_1$-$C_4$alkoxy, $C_1$-$C_4$haloalkyl, nitro or cyano, and
$R_3$ and $R_4$, together with the nitrogen atom to which they are attached, also form a 5- or 6-membered heterocyclic ring system which may contain an additional oxygen or sulfur atom in the ring.

17 Claims, No Drawings

CYCLOHEXANEDIONECARBOXYLIC ACID DERIVATIVES WITH HERBICIDAL AND PLANT GROWTH REGULATING PROPERTIES

CROSS-REFERENCE TO RELATED APPLICATION

This is a continuation-in-part of application Ser. No. 610,222 filed May 14, 1984.

The present invention relates to novel cyclohexanedionecarboxylic acid derivatives with herbicidal and plant growth regulating properties, to compositions which contain them, and to the use of said derivatives for selective and total weed control and for regulating plant growth.

The novel cyclohexanedionecarboxylic acid derivatives have the formula I

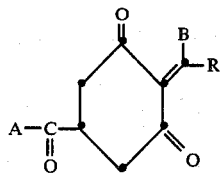

(I)

wherein

A is an $-OR_2$ or $-NR_3R_4$ radical,

B is hydroxy, an $-NHOR_1$ radical or a metal or ammonium salt thereof

R is $C_1-C_6$alkyl or $C_3-C_6$cycloalkyl, each unsubstituted or substituted by halogen, $C_1-C_6$alkoxy or $C_2-C_4$alkythio, $R_1$ is $C_1-C_6$alkyl, $C_1-C_6$haloalkyl, $C_3-C_6$alkenyl, $C_3-C_6$haloalkenyl or $C_3-C_6$alkynyl, $R_2$, $R_3$ and $R_4$ are each independently hydrogen, $C_1-C_6$alkyl, $C_1-C_6$haloalkyl, $C_2-C_{10}$alkoxyalkyl, $C_2-C_{10}$alkylthioalkyl; $C_3-C_6$alkenyl which is unsubstituted or substituted by halogen, $C_1-C_4$alkoxy or $C_1-C_4$alkylthio; $C_3-C_6$alkynyl; phenyl or $C_1-C_6$aralkyl, wherein the phenyl nucleus is unsubstituted or substituted by halogen, $C_1-C_4$alkyl, $C_1-C_4$alkoxy, $C_1-C_4$haloalkyl, nitro or cyano, and $R_3$ and $R_4$, together with the nitrogen atom to which they are attached, also form a 5- or 6-membered heterocyclic ring system which may contain an additional oxygen or sulfur atom in the ring.

In the above definitions the alkyl radicals comprise both straight chain and branched radicals, e.g. methyl, ethyl, propyl, isopropyl, butyl, isobutyl, sec-butyl, tert-butyl, as well as all stereoisomers of the higher homologues. Alkenyl and alkynyl also comprise straight chain and branched radicals, e.g. vinyl, allyl, methallyl, butenyl, methylbutenyl and dimethylbutenyl, ethynyl, propynyl, butynyl, methylbutynyl and dimethylbutynyl.

Halogen is fluorine, chlorine, bromine or iodine.

A 5- or 6-membered heterocyclic ring system $-NR_3R_4$ which may contain an additional oxygen or sulfur atom in the ring is pyrrole, pyrolidine, piperidine, morpholine or also thiomorpholine. These rings may also be substituted by methyl.

The salts of these compounds are obtained with bases. Suitable bases are preferably alkali metal hydroxides, alkaline earth metal hydroxides, iron, copper, nickel and zinc hydroxides, and also ammonia or quarternary $C_1-C_4$alkylammonium or $C_1-4$hydroxyalkylammonium bases.

The cyclohexanedionecarboxylic acid derivatives of the formula I have good herbicidal and plant growth regulating properties. Particularly effective compounds comprise the following groups:

cyclohexanederivatives of the formula Ia

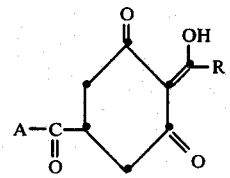

(Ia)

wherein A and R are as defined above, and the salts thereof, preferably metal and ammonium salts;

the derivatives of the formula Ia, wherein A is an $-OR_2$ radical and R and $R_2$ are as defined above, and the metal and ammonium salts thereof;

the derivatives of the formula Ia, wherein A is an $-NR_3R_4$ radical and R, $R_3$ and $R_4$ are as defined above, and the metal and ammonium salts thereof;

the derivatives of the formula Ia, wherein A is as defined above and R is a $C_3-C_6$cycloalkyl radical, and the metal and ammonium salts thereof.

Further useful compounds are the cyclohexanediones of the formula Ib

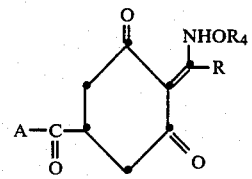

(Ib)

wherein A, R and $R_1$ are as defined above, and the metal and ammonium salts therof;

the derivatives of the formula Ib, wherein A is an $-OR_2$ radical and R, $R_1$ and $R_2$ are as defined above, and the metal and ammonium salts thereof;

the derivatives of the formula Ib, wherein A is an $-NR_3R_4$ radical and R, $R_1$, $R_3$ and $R_4$ are as defined above, and the metal and ammonium salts thereof.

Preferred individual compounds are:

ethyl 4-butyryl-3,5-cyclohexanedionecarboxylate,
isobutyl 4-butyryl-3,5-cyclohexandionecarboxylate,
ethyl 4-(1-ethoxyaminobutylidene)-3,5-cyclohexanedionecarboxylate,
ethyl 4-(1-allyloxyaminobutylidene)-3,5-cyclohexanedionecarboxylate,
ethyl 4-(cyclopropylhydroxymethylidene)-3,5-cyclohexanedionecarboxylate,
dimethyl 4-(1-ethoxyaminobutylidene)-3,5-cyclohexanedionecarboxamide,
dimethyl 4-(1-allyloxyaminobutylidene)-3,5-cyclohexanedionecarboxamide, and the sodium, ammonium and tetramethylammonium salts thereof.

The cyclohexanedionecarboxylic acid derrivatives of the formula I can be obtained in different tautomeric forms. For example, methyl 4-(1-ethoxyaminobutylidene)-3,5-cyclohexandionecarboxylate is obtained in the following forms:

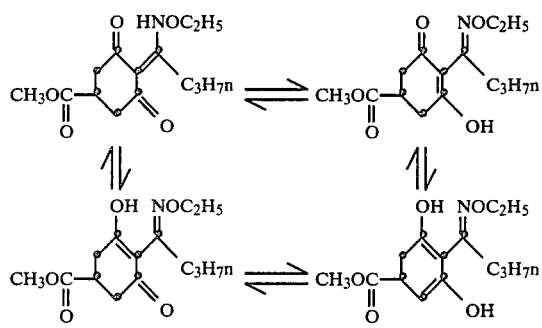

The cyclohexanedionecarboxylates of the formula I are prepared in conventional manner by reacting a 3,5-cyclohexanedionecarboxylic acid derivative of the formula II

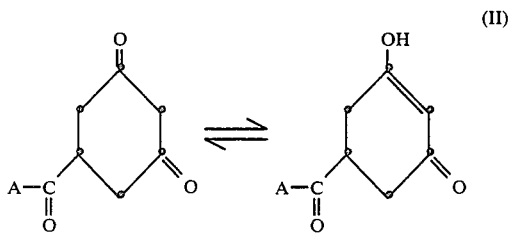

wherein A is an ester or amide radical as defined above, with an acid halide of the formula III Hal—COR (III)

wherein R is as defined above, in an inert organic solvent and in the presence of a base as acid acceptor, isolating the product so obtained and, if desired, reacting it further with a hydroxylamine of the formula IV

HONHR₁ (IV)

wherein R₁ is as defined above, in an inert water-immiscible solvent at boiling temperature under condensation conditions, and isolating the resultant product.

The compounds of formula II react also with their enolic hydroxide group. This group has either to be liberated again by acid hydrolysis from the condensed —OCOR-rest or else it has to be protected previously by etherification e.g. in an acid medium in the presence of a water absorber, like concentrated sulfuric acid, destillation on a water-separated fitted preferably with a molecular sieve or with N,N-dicyclohexylcarbonimide.

The preparation of these intermediates is known e.g. from J. Am. Chem. Soc. 78 (1956) 4405 and 81 (1958) 4278 or also from the published Japanese Patent Application JA-A 57-47947.

Some of these intermediates are new. They correspond to the formula V

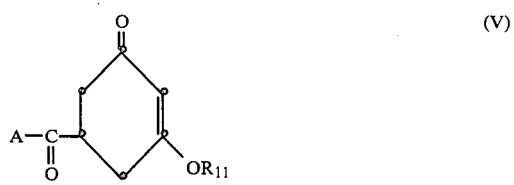

wherein A is defined as above under formula I and R¹¹ is selected from among C₁-C₆ haloalkyl, C₃-C₆ alkenyl, C₃-C₆ haloalkenyl, C₃-C₆ alkinyl, C₂-C₁₀ alkoxyalkyl and C₂-C₁₀ alkoxyalkenyl and are part of this invention.

Suitable solvents for these reactions are in particular aromatic hydrocarbons such as benzene, toluene and xylene, and also halogenated hydrocarbons such as chloroform, dichloroethane and carbon tetrachloride.

The reaction temperatures are in the range from room temperature to the boiling point of the reaction mixture. During the addition of acid chloride it may be necessary to cool the reaction vessel.

Suitable acid acceptors are organic and inorganic bases, e.g. pyridine, 4-aminopyridine, collidine, triethylamine, ammonium, and sodium, potassium or calcium carbonate or the corresponding bicarbonates.

Suitable acid halides of the formula III are mainly acetyl chloride, propionyl chloride, butyryl chloride, valeryl chloride, 3-methoxypropionyl chloride, 2-chloropropionyl chloride, cyclopropanoyl chloride or cyclohexanoyl chloride, and also the corresponding bromides.

Suitable hydroxylamines of the formula IV are in particular the methyl-, ethyl-, chloroethyl-, propyl-, isopropyl-, butyl-, isobutyl-, allyl-, cycloallyl-, methallyl- and propynylhydroxylamines, which may also be used in salt form, e.g. as hydrochloride.

The starting cyclohexanedionecarboxylic acid derivatives of the formula II are obtained on the one hand by hydrogenating 3,5-dihydroxybenzoic acid with hydrogen and Raney nickel and subsequently esterifying or amidating the acid radical in accordance with the following reaction scheme:

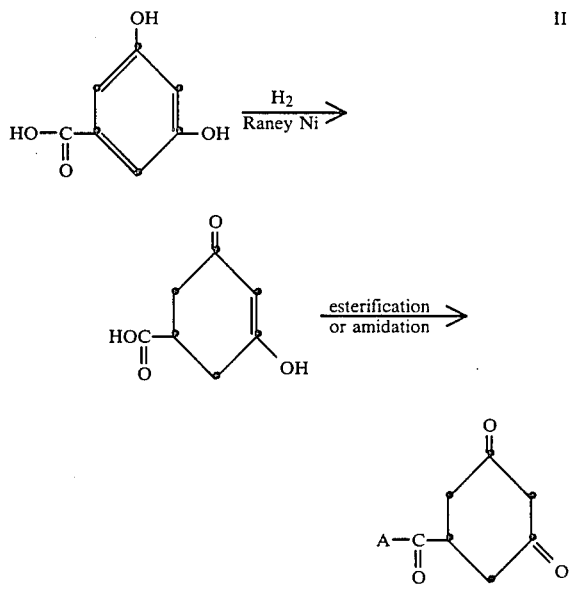

In the above reaction the keto group must be protected, e.g. as enol ether or enamine, q.v. J. Am. Chem. Soc. 78, 4405 (1956).

However, it is also possible to hydrogenate a 3,5-dihydroxybenzoic acid derivative with hydrogen and Raney nickel in accordance with the reaction scheme:

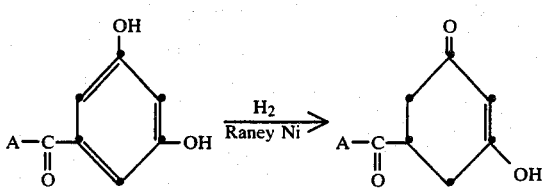

q.v. Arch. Pharm. 307, 577 (1974).

When used at low rates of application, the compounds of formula I have good selective growth inhibiting and selective herbicidal properties which make them most suitable for use in crops of useful plants, especially in sugar cane, cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used at very low rates of application.

In addition the compounds of formula I have pronounced growth-regulating properties which can result in an increase in the yield of cultivated plants or harvested crops. Further, many compounds of formula I have a growth inhibiting action which is dependent on the concentration. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able to promote flower formation and fruiting to a greater extent, whilst vegetative growth is inhibited.

Inhibition of the vegetative growth of monocot plants, e.g. grasses or also cultivated plants such as cereals, is sometimes desirable and advantageous. Such a growth inhibition is of economic interest, inter alia, in respect of grasses, as the frequency of cutting in flower gardens, parks, sport fields or road shoulders can thereby be reduced. Of importance too is the inhibition of growth of herbaceous and ligneous plants on road shoulders and near transmission lines, or quite generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals and this too counteracts lodging.

Further, the compounds of formula I are suitable for preventing stored potatoes from seeding. During winter storage, potatoes often develop sprouts which result in shrinkage, weight loss, and rot.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, as compositions together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts or higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstitued or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, and phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I–III, Chemical Publishing Co., New York, 1980–81.

The compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

Emulsifiable concentrates active ingredient: 1 to 20%, preferably 5 to 10%
surfactant: 5 to 30%, preferably 10 to 20%
liquid carrier: 50 to 94%, preferably 70 to 85%

Dusts active ingredient: 0.1 to 10%, preferably 0.1 to 1%
solid carrier: 99.9 to 90%, preferably 99.9 to 99%

Suspension concentrates active ingredient: 5 to 75%, preferably 10 to 50%
water: 94 to 25%, preferably 90 to 30%
surfactant: 1 to 40%, preferably 2 to 30%

Wettable powders active ingredient: 0.5 to 90%, preferably 1 to 80%
surfactant: 0.5 to 20%, preferably 1 to 15%
solid carrier: 5 to 95%, preferably 15 to 90%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further auxiliaries such as stabilisers, antifoams, viscosity regulators, binders, tackifiers, as well as fertilisers and other compounds for obtaining special effects.

The invention is illustrated by the following Examples.

Preparatory Examples

EXAMPLE 1

Preparation of isobutyl 4-butyryl-3,5-cyclohexanedionecarboxylate

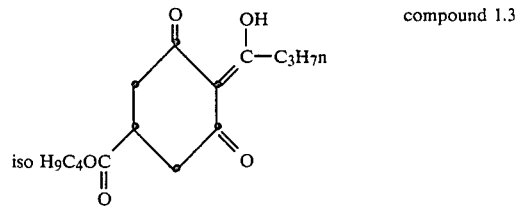

compound 1.3

(a) Isobutyl 3,5-cyclohexanedionecarboxylate

A mixture of 50 g of 3,5-cyclohexanedionecarboxylic acid, 150 ml of isobutanol, 30 g of 85% orthophosphoric acid and 400 ml of toluene is boiled overnight in a water separator. The solution is then concentrated in a rotovap. The residue is taken up in 200 ml of tetrahydrofuran, and the solution is boiled for 2 hours after addition of 100 ml of 1N hydrochloric acid. The cooled solution is extracted with ethyl acetate and the organic phase is separated, washed with a saturated solution of sodium chloride, dried and concentrated. The wax-like residue is recrystallised from ether/hexane and the crystalline product melts at 74°–76° C. (compound 3.22).

(b) Isobutyl 4-butyryl-3,5-cyclohexanedionecarboxylate 30 ml of butyryl chloride are added dropwise to a solution of 60 g of isobutyl 3,5-cyclohexanedionecarboxylate and 25 ml of pyridine in 400 ml of dichloroethane, and the mixture is stirred for a further 15 hours at room temperature. The reaction solution is then filtered and the filtrate is washed with 1N hydrochloric acid, dried and concentrated. The O-acylated product so obtained is taken up in 200 ml of dichloroethane, 4 g of 4-dimethylaminopyridine are added, and the reaction mixture is refluxed for 4 hours. The cooled reaction solution is then washed with 1N hydrochloric acid, dried, concentrated, and the residue is chromatographed over a small amount of silica gel, affording 51 g of isobutyl 4-butyryl-3,5-cyclohexanedionecarboxylate as a pale oil with a refractive index of $n_D^{21} 1.4907$.

EXAMPLE 2

Preparation of isobutyl 4-(1-allyloxyaminobutylidene)-3,5-cyclohexanedionecarboxylate

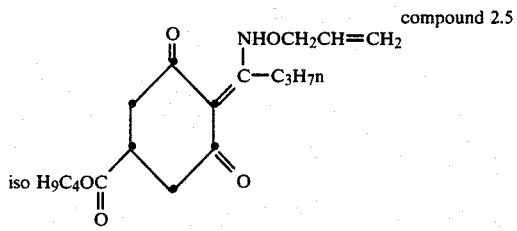

compound 2.5

A mixture of 14 g of isobutyl 4-butyryl-3,5-cyclohexanedionecarboxylate, 6.5 g of O-allylhydroxylamine hydrochloride, 6.5 g of potassium carbonate and 150 ml of chloroform is refluxed for 6 hours. The reaction solution is then washed with 1N hydrochloric acid, dried, concentrated, and the residue is chromatographed over a small amount of silica gel with a 1:3 mixture of ethyl acetate/hexane. The solvent is removed by evaporation, leaving as residue 6.9 g of isobutyl 4-(1-allyloxyaminobutylidene)-3,5-cyclohexanedionecarboxylate as a pale oil with a refractive index of $n_D^{21} = 1.4989$.

EXAMPLE 3

Preparation of dimethyl 4-(1-ethoxyaminobutylidene)-3,5-cyclohexanedionecarboxamide

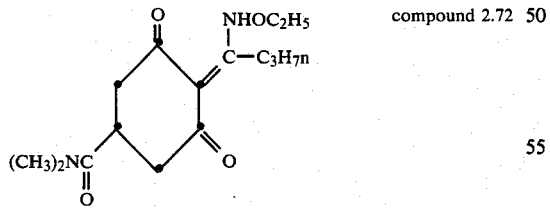

compound 2.72

(a) With stirring, 18.4 ml of dimethylcarbamoyl chloride are added dropwise to a solution of 15.6 g of 3,5-cyclohexanedioncarboxylic acid and the mixture is then stirred for a further 12 hours at room temperature and for 2 hours at boiling temperature under reflux. The cooled reaction mixture is then taken up in 400 ml of ethyl acetate and the organic phase is washed with 4 times with brine, dried over magnesium sulfate and concentrated. The residue consists of 13.2 g of crude dimethyl 3-(N,N-dimethylcarbamoyl)-5-oxocyclohex-(3)-enecarboxamide. The crude residue is dissolved in 300 ml of tetrahydrofuran, 8 ml of concentrated hydrochloric acid are added and the solution is stirred for 2 hours at room temperature. The reaction mixture is then washed with brine, dried over magnesium sulfate and concentrated, affording 13.2 g of dimethyl 3,5-cyclohexandionecarboxamide as a resinous substance. Purification by chromatography with hexane/ether over a column of silica gel yields crystals with a melting point of 152°–155° C. (compound 3.02).

(b) The 13.2 g of dimethyl cyclohexanedionecarboxamide obtained in (a) are dissolved in 100 ml of ethylene chloride together with 6.9 ml of pyridine. With stirring, 8.5 ml of butyryl chloride are added dropwise to this solution. The ensuing reaction is slightly exothermic. The resultant yellow suspension is stirred for 14 hours at room temperature, then washed with 1N hydrochloric acid and brine, dried over magnesium sulfate and concentrated. The residue is dissolved in 100 ml of dichloroethane and refluxed for 2 hours together with 0.5 g of 4-dimethylaminopyridine and 0.1 ml of butyryl chloride. The cooled reaction mixture is subsequently washed with 20 ml of 1N hydrochloric acid saturated with sodium chloride, dried over magnesium sulfate and concentrated. The residue is purified by chromatography over a column of silica gel with ethyl acetate as eluant, affording 7.8 g of dimethyl 4-butyryl-3,5-cyclohexanedionecarboxamide as a pale oil.

(c) A mixture of 4.3 g of dimethyl the 4-butyryl-3-cyclohexanedionecarboxamide obtained in (b), 1.9 g of ethoxyamine hydrochloride, 1.4 g of potassium carbonate in 50 ml of chloroform and 5 ml of methanol is stirred for 24 hours at room temperature. The reaction mixture is then washed with 1N hydrochloric acid, dried over magnesium sulfate and concentrated. The residue is an oil which is purified by chromatography over a column of silica gel with ethyl acetate as eluant. The solvent is removed by evaporation and the residue is an oil which crystallises on standing. Yield: 2 g of the title compound with a melting point of 54°–58° C.

EXAMPLE 4

Preparation of benzyl 4-(ethoxyaminobutylidene)-3,5-cyclohexanedionecarboxamide

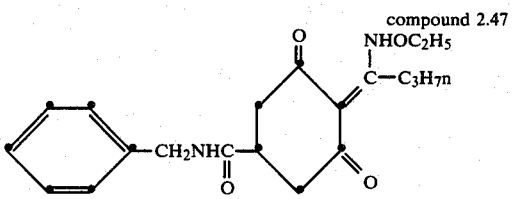

compound 2.47

(a) A solution of 107 g of 3,5-cyclohexanedionecarboxylic acid and 1 ml of concentrated sulfuric acid in 400 ml of methanol is stirred for 3 hours at room temperature. A crystalline solid precipitates during stirring. Then 400 ml of ether are added and crystals of 3-methoxy-5-oxo-cyclohex-3-ene-carboxylic acid precipitate. The precipitate is isolated by filtration and dried in an exsiccator, affording 120 g of 3-methoxy-5-oxocyclohex-3-ene-1-carboxylic acid. oil.

(b) 34 g of 3-methoxy-5-oxo-cyclohex-3-ene-carboxylic acid, 33 g of N,N'-carbonyl diimidazole and 300 ml of dichloroethane are mixed and the resultant suspension is stirred for 1 hour at room temperature. The 22 ml of benzylamine are added dropwise and stirring is continued for 14 hours (overnight) at room temperature. Then 1N hydrochloric acid is added to the reaction mixture until the pH is between 3 and 4. The organic phase is separated, washed with brine, dried over magnesium sulfate and concentrated, affording 43.6 g of benzyl 3-methoxy-5-oxy-cyclohex-3-ene-carboxamide as a pale oil (comound 3.01).

(c) 42 g of the above benzyl 3-methoxy-5-oxy-5-oxy-cyclohex-3-ene-carboxamide are dissolved in 500 ml of tetrahydrofuran. Then 0.5 ml of concentrated hydrochloric acid and 10 ml of water area added and the mixture is stirred for 5 hours at room temperature. The solution is dried over a molecular sieve, affording 16.6 g of crystalline benzyl 3,5-cyclohexanedionecarboxamide. A further 17.8 g of product can be obtained by concentrating the mother liquor. Yield: 34.4 g. Melting point: 178°–181° C.

(d) 29 g of benzyl 3,5-cyclohexanedionecarboxamide are reacted with butyryl chloride in ethylene chloride in the presence of a small amount of pyridine in accordance with Example 3b. The reaction mixture is worked up and benzyl 4-buryryl-3,5-cyclohexanedionecarboxamide is obtained as a wax-like substance which is crystallised from ether/hexane. Yield: 15 g. Melting point: 126°–128° C.

(e) 6 g of benzyl 4-butyryl-3,5-cyclohexanedionecarboxamide are reacted with ethoxyamine hydrochloride in chloroform in the presence of potassium carbonate in accordance with Example 3c. The reaction mixture is worked up, affording 2.3 g of crystalline benzyl 4-(1-ethoxyaminobutylidene)-3,5-cyclohexanedionecarboxamide with a melting point of 88°–90° C.

The following compounds are prepared by procedures analogous to those described in the foregoing Examples:

TABLE 1

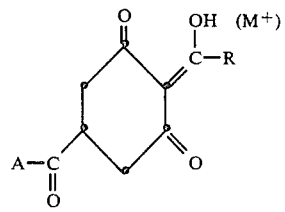

| No. | A | R | $M^{\oplus}$ | Physical data |
|---|---|---|---|---|
| 1.1 | $OCH_3$ | $C_3H_7n$ | | |
| 1.2 | $OC_2H_5$ | $C_3H_7n$ | | $n_D^{27}$ 1.5060 |
| 1.3 | $OC_4H_9iso$ | $C_3H_7n$ | | $n_D^{27}$ 1.4907 Example 1 |
| 1.4 | $OCH_2SCH_3$ | $C_3H_7n$ | | $n_D^{25}$ 1.5193 |
| 1.5 | $OC_2H_4SCH_3$ | $C_3H_7n$ | | |
| 1.6 | $OC_2H_4OCH_3$ | $C_3H_7n$ | | |
| 1.7 | $OC_3H_7i$ | $C_3H_7n$ | | |
| 1.8 | $OC_3H_6Cl$ | $C_3H_7n$ | | $n_D^{25}$ 1.4998 |
| 1.9 | $OCH_2$-furyl | $C_3H_7n$ | | |
| 1.10 | $OCH_2$-(methoxy)furyl | $C_3H_7n$ | | |
| 1.11 | $OCH_2CH{=}CH_2$ | $C_3H_7n$ | | |
| 1.12 | $OCH_2CCl{=}CH_2$ | $C_3H_7n$ | | |
| 1.13 | $OCH_2C{\equiv}CH$ | $C_3H_7n$ | | |
| 1.14 | $OCH_3$ | $C_6H_{13}n$ | | |
| 1.15 | $OC_2H_5$ | cyclopropyl | | $n_D^{30}$ 1.5330 |
| 1.16 | $OCH_3$ | cyclohexyl | | |
| 1.17 | $OC_6H_{13}$ | $CH_3$ | | |
| 1.18 | $OCH_2SCH_3$ | $CH_3$ | | |
| 1.19 | $OC_2H_5$ | $CH_2SCH_3$ | | |
| 1.20 | $OC_2H_5$ | $C_2H_4OCH_3$ | | |
| 1.21 | $OC_4H_9tert.$ | $CHClCH_3$ | | |
| 1.22 | $NH_2$ | $C_3H_7n$ | | m.p. 167–169° |
| 1.23 | $NH_2$ | $C_2H_5n$ | | |
| 1.24 | $N(CH_3)_2$ | $C_3H_7n$ | | |
| 1.25 | $N(CH_3)_2$ | $C_3H_7i$ | | |
| 1.26 | $NHC_4H_9iso$ | $C_3H_7n$ | | m.p. 126–128° |
| 1.27 | $NHC_4H_9iso$ | $CH_3$ | | |
| 1.28 | $N(CH_2{-}CH{=}CH_2)_2$ | cyclopropyl | | |

TABLE 1-continued $$\text{structure with } A-C(=O)-\text{cyclohexanedione} = C(OH)(M^+)-R$$

| No. | A | R | M⊕ | Physical data |
|---|---|---|---|---|
| 1.30 | NHCH₂—C₆H₅ | C₃H₇n | | |
| 1.31 | NHCH₂—C₆H₄—NO₂ | C₂H₄Cl | | |
| 1.32 | N(CH₃)CH₂—C₆H₅ | C₂H₄OC₂H₅ | | |
| 1.33 | NHC₂H₄SC₂H₅ | C₄H₉iso | | |
| 1.34 | piperidino | C₃H₇iso | | |
| 1.35 | morpholino | C₆H₁₃n | | |
| 1.36 | OC₂H₅ | C₃H₇n | Na⁺ | |
| 1.37 | OC₂H₅ | C₃H₇n | NH₄⁺ | |
| 1.38 | OC₄H₉iso | C₃H₇n | ½Mg⁺ | |
| 1.39 | OC₄H₉iso | C₃H₇n | ½Zn⁺ | |
| 1.40 | N(CH₃)₂ | C₃H₇n | N(CH₃)₄⁺ | |
| 1.41 | NH₂ | C₂H₅ | Na⁺ | |
| 1.42 | OC₂H₅ | CH₃ | | m.p. 49–51° |
| 1.43 | OC₂H₅ | cyclobutyl | | |
| 1.44 | OCH₃ | cyclobutyl | | |
| 1.45 | OC₂H₅ | cyclopentyl | | |
| 1.46 | OCH₃ | cyclopentyl | | |
| 1.47 | OC₂H₅ | cyclohexyl | | |
| 1.48 | OCH₃ | cyclohexyl | | |
| 1.49 | N(CH₃)₂ | cyclopropyl | | m.p. 109–112° (wax) |
| 1.50 | NHCH₂—C₆H₅ | cyclopropyl | | m.p. 130–144° (wax) |
| 1.51 | NH—C₆H₅ | cyclopropyl | | |
| 1.52 | NH—C₆H₄—CF₃ | cyclopropyl | | |
| 1.53 | N(CH₃)OCH₃ | C₃H₇n | | oil |
| 1.54 | N(CH₃)OCH₃ | C₂H₅ | | |
| 1.55 | NH—C₆H₅ | C₃H₇n | | m.p. 123–127° |

TABLE 1-continued

[Structure: cyclohexane-1,3-dione with =C(OH)-R substituent at position 2, and A-C(=O)- substituent at position 5; (M+)]

| No. | A | R | M⊕ | Physical data |
|---|---|---|---|---|
| 1.56 | NH-C₆H₅ (phenyl) | CH₃ | | |
| 1.57 | NH-C₆H₅ | $C_6H_{13}n$ | | |
| 1.58 | NH-C₆H₅ | $C_2H_4CH(CH_3)_2$ | | |
| 1.59 | NH-phenyl-CF₃ | $C_3H_7n$ | | |
| 1.60 | NH-phenyl-OCH₃ | $C_3H_7n$ | | |
| 1.61 | NH-phenyl-Cl | CH₃ | | |
| 1.62 | $N(C_2H_5)_2$ | $C_3H_7n$ | | oil |
| 1.63 | $NHCH_3$ | $C_3H_7n$ | | |
| 1.64 | $N(CH_3)$-phenyl | $C_3H_7n$ | | |
| 1.65 | cyclopropylamino | $C_3H_7n$ | | |
| 1.66 | $NHC_6H_{13}n$ | $C_3H_7n$ | | |
| 1.67 | $NHC_2H_4SCH_3$ | $C_3H_7n$ | | wax |
| 1.68 | $NHC_2H_4SCH_3$ | $C_2H_5$ | | |
| 1.69 | $NHC_2H_4SC_3H_7i$ | $C_3H_7n$ | | |
| 1.70 | azetidinyl (N-cyclobutyl ring) | $C_3H_7n$ | | wax |
| 1.71 | $N(CH_2CH=CH_2)_2$ | $C_3H_7n$ | | oil |
| 1.72 | $N(CH_3)_2$ | cyclobutyl | | |
| 1.73 | $N(CH_3)_2$ | $C_6H_{13}n$ | | |
| 1.74 | $N(CH_3)_2$ | $C_2H_5$ | | m.p. 82–83° |
| 1.75 | $NHCH_3$ | $C_5H_{11}n$ | | |
| 1.76 | $N(CH_3)C_2H_5$ | $C_3H_7n$ | | |
| 1.77 | $N(CH_3)C_2H_5$ | $C_3H_7i$ | | |
| 1.78 | $N(CH_3)C_2H_5$ | cyclopropyl | | |
| 1.79 | $N(CH_3)_2$ | $C_5H_{11}n$ | | m.p. 70–72° |

TABLE 2

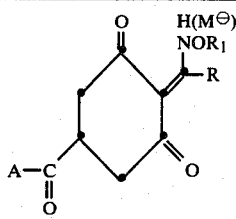

| No. | A | R | $R_1$ | $M^\oplus$ | Physical data |
|---|---|---|---|---|---|
| 2.1 | $OCH_3$ | $C_3H_7n$ | $C_3H_5$ | | |
| 2.2 | $OC_2H_5$ | $C_3H_7n$ | $C_2H_5$ | | $n_D^{27}$ 1.5002 |
| 2.3 | $OC_2H_5$ | $C_3H_7n$ | $CH_2CH=CH_2$ | | $n_D^{27}$ 1.5112 |
| 2.4 | $OC_4H_9$iso | $C_3H_7n$ | $C_2H_5$ | | $n_D^{27}$ 1.4929 |
| 2.5 | $OC_4H_9$iso | $C_3H_7n$ | $CH_2CH=CH_2$ | | $n_D^{27}$ 1.4989 Example 2 |
| 2.6 | $OCH_2SCH_3$ | $C_3H_7n$ | $C_2H_5$ | | $n_D^{25}$ 1.5198 |
| 2.7 | $OCH_2SCH_3$ | $C_3H_7n$ | $CH_2-C\equiv CH$ | | |
| 2.8 | $OC_3H_7$iso | $C_3H_7n$ | $C_2H_5$ | | $n_D^{25}$ 1.5003 |
| 2.9 | $OC_3H_7$iso | $C_3H_7n$ | $CH_2-CH=CH_2$ | | $n_D^{25}$ 1.5088 |
| 2.10 | $OC_3H_7$iso | $C_3H_7n$ | $CH_2CCl=CH_2$ | | |
| 2.11 | $OC_2H_4SCH_3$ | $C_3H_7n$ | $C_2H_5$ | | |
| 2.12 | $OC_2H_4SCH_3$ | $C_3H_7n$ | $CH_2-CH=CH_2$ | | |
| 2.13 | $OC_2H_4SCH_3$ | $C_3H_7n$ | $C_2H_4Cl$ | | |
| 2.14 | $OC_2H_4OCH_3$ | $C_3H_7n$ | $CH_3$ | | |
| 2.15 | $OC_2H_4OCH_3$ | $C_3H_7n$ | $C_2H_5$ | | |
| 2.16 | $OC_3H_6Cl$ | $C_3H_7n$ | $C_2H_5$ | | |
| 2.17 | $OCH_2$-phenyl | $C_3H_7n$ | $C_2H_5$ | | |
| 2.18 | $OCH_2$-phenyl | $C_3H_7n$ | $CH_2-CH=CH_2$ | | |
| 2.19 | $OCH_2$-phenyl-$OCH_3$ | $C_3H_7n$ | $C_6H_{13}n$ | | |
| 2.20 | $OCH_2CH=CH_2$ | $C_3H_7n$ | $C_6H_{13}n$ | | |
| 2.21 | $OCH_2-CH=CH_2$ | $C_3H_7n$ | $CH_3$ | | |
| 2.22 | $OC_2H_4Cl$ | $C_3H_7n$ | $CH_2-C\equiv CH_2$ | | |
| 2.23 | $OCH_2CCl=CH_2$ | $C_3H_7n$ | $C_2H_4Cl$ | | |
| 2.24 | $OCH_2-C\equiv CH$ | $C_3H_7n$ | $C_6H_{13}$iso | | |
| 2.25 | $OCH_3$ | $C_6H_{13}n$ | $C_2H_5$ | | |
| 2.26 | $OC_2H_5$ | cyclopropyl | $CH_2CH=CH_2$ | | |
| 2.27 | $OCH_3$ | cyclohexyl | $C_2H_5$ | | |
| 2.28 | $OC_6H_{13}n$ | $CH_3$ | $C_4H_9n$ | | |
| 2.29 | $OCH_2SCH_3$ | $CH_3$ | $C_4H_9$sec | | |
| 2.30 | $OC_2H_5$ | $CH_2SCH_3$ | $C_2H_5$ | | |
| 2.31 | $OC_2H_5$ | $C_2H_4OCH_3$ | $CH_2-C\equiv CH$ | | |
| 2.32 | $OC_4H_9$tert. | $CHCl-CH_3$ | $C_2H_5$ | | |
| 2.33 | $NH_2$ | $C_3H_7n$ | $C_2H_5$ | | |
| 2.34 | $NH_2$ | $C_3H_7n$ | $CH_2-CH=CH_2$ | | m.p. 127–129° |
| 2.35 | $NH_2$ | $C_2H_5$ | $C_2H_5$ | | |
| 2.36 | $NH_2$ | $C_2H_5$ | $CH_2-CCl=CH_2$ | | |
| 2.37 | $N(CH_3)_2$ | $C_3H_7n$ | $C_2H_5$ | | m.p. 54–58° |
| 2.38 | $N(CH_3)_2$ | $C_3H_7i$ | $CH_2-CH=CH_2$ | | m.p. 59–65° |
| 2.39 | $N(CH_3)_2$ | $C_3H_7i$ | $CH_3$ | | |
| 2.40 | $N(CH_3)_2$ | $C_3H_7i$ | $C_3H_6Br$ | | |
| 2.41 | $NHC_4H_9$iso | $C_3H_7n$ | $C_2H_5$ | | m.p. 88–90° |
| 2.42 | $NHC_4H_9$iso | $C_3H_7n$ | $CH_3$ | | |
| 2.43 | $NHC_4H_9$iso | $C_3H_7n$ | $CH_2CH=CH_2$ | | m.p. 100–102° |
| 2.44 | $NHC_4H_9$iso | $CH_3$ | $CH_2C\equiv CH$ | | |
| 2.45 | $N(CH_2-CH=CH_2)_2$ | cyclopropyl | $C_2H_5$ | | |
| 2.46 | $NHCH_2-C\equiv CH$ | $CH_2OCH_3$ | $C_5H_{11}$sec | | |

TABLE 2-continued

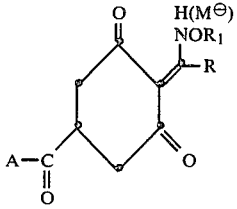

| No. | A | R | R₁ | M⊕ | Physical data |
|---|---|---|---|---|---|
| 2.47 | 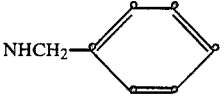 NHCH₂— | $C_3H_7n$ | $C_2H_5$ | | m.p. 116–119° Example 14 |
| 2.48 | 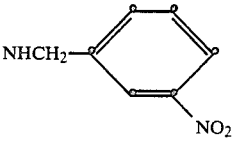 NHCH₂— (NO₂) | $C_2H_4Cl$ | $C_2H_4F$ | | |
| 2.49 | 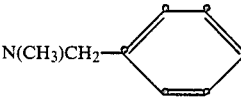 N(CH₃)CH₂— | $C_2H_4OC_2H_4$ | $CH_2CF_3$ | | |
| 2.50 | $NHC_2H_4OCH_3$ | $C_3H_7n$ | $C_2H_5$ | | |
| 2.51 | $NHC_2H_4SCH_3$ | $C_4H_9iso$ | $CH_3$ | | |
| 2.52 | piperidino | $C_3H_7i$ | $CH_2-CH=CH_2$ | | |
| 2.53 | morpholino | $C_6H_{13}$ | $C_2H_5$ | | |
| 2.54 | $OC_2H$ | $C_3H_7n$ | $C_2H_5$ | $Na^+$ | |
| 2.55 | $OC_2H_5$ | $C_3H_7n$ | $CH_2-CH=CH_2$ | $K^+$ | |
| 2.56 | $OC_4H_9iso$ | $C_3H_7n$ | $C_2H_5$ | $\frac{1}{2}Cu^{++}$ | |
| 2.57 | $OC_4H_9iso$ | $C_3H_7n$ | $CH_2-CH=CH_2$ | $NH_4^+$ | |
| 2.58 | $N(CH_3)_2$ | $C_3H_7n$ | $CH_2-CH=CH_2$ | $Na^+$ | |
| 2.59 | $NH_2$ | $C_2H_5$ | $CH_2-CCl=CH_2$ | $N(C_4H_9n)_4^+$ | |
| 2.60 | $OC_2H_5$ | $CH_3$ | $C_2H_5$ | | $n_D^{30}$ 1.5077 |
| 2.61 | $N(CH_3)OCH_3$ | $C_3H_7n$ | $C_2H_5$ | | $n_D^{25}$ 1.5122 |
| 2.62 | $N(CH_3)OCH_3$ | $C_3H_7n$ | $CH_2CH=CH_2$ | | |
| 2.63 | $N(CH_3)OCH_3$ | $C_3H_7n$ | $CH_2CH=CHCl$ | | oil |
| 2.64 | $N(C_2H_5)_2$ | $C_3H_7n$ | $C_2H_5$ | | wax |
| 2.65 | $N(C_2H_5)_2$ | $C_3H_7n$ | $CH_2CH=CH_2$ | | |
| 2.66 | $N(CH_3)_2$ | cyclopropyl | $C_2H_5$ | | |
| 2.67 | 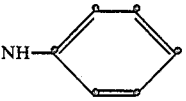 NH— | cyclopropyl | $CH_2CH=CH_2$ | | |
| 2.68 | $N(CH_3)OCH_3$ | $C_2H_5$ | $C_2H_5$ | | |
| 2.69 | 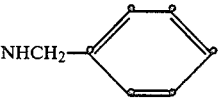 NHCH₂— | $C_4H_9iso$ | $C_2H_5$ | | |
| 2.70 |  NHCH₂— | cyclopropyl | $CH_2CH=CH_2$ | | |
| 2.71 |  NH— | $C_3H_7n$ | $C_2H_5$ | | |

TABLE 2-continued $$\text{structure: cyclohexane-1,3-dione with A-C(=O)- at 5-position and =C(R)-NOR}_1\text{ (with H(M}^\ominus\text{)) at 2-position}$$

| No. | A | R | R₁ | M⊕ | Physical data |
|---|---|---|---|---|---|
| 2.72 | 4-NH-phenyl | $C_3H_7n$ | $CH_2CH=CH_2$ | | wax Example 3 |
| 2.73 | 4-NH-phenyl | $CH_3$ | $CH_2CH=CH_2$ | | |
| 2.74 | 4-NH-phenyl | $C_{16}H_{13}n$ | $C_2H_5$ | | |
| 2.75 | 4-NH-phenyl-4-CF₃ | $C_3H_7n$ | $C_2H_5$ | | |
| 2.76 | 4-NH-phenyl-4-OCH₃ | $C_6H_{13}n$ | $C_2H_5$ | | |
| 2.77 | 4-NH-phenyl-4-Cl | $C_6H_{13}$ | $CH_2CH=CH_2$ | | |
| 2.78 | 4-N(CH₃)-phenyl | $C_6H_{13}n$ | $CH_2CH=CH_2$ | | |
| 2.79 | cyclopropylamino | $C_6H_{13}n$ | $C_2H_5$ | | |
| 2.80 | $NHC_6H_{13}n$ | $CH_3$ | $C_2H_5$ | | |
| 2.81 | 4-NH-phenyl | $C_3H_7n$ | $CH_2CH=CHCl$ | | |
| 2.82 | $N(CH_3)_2$ | $C_3H_7n$ | $CH_2CH=CHCl$ | | |
| 2.83 | 4-NHCH₂-phenyl | $C_3H_7n$ | $CH_2CH=CHCl$ | | |
| 2.84 | $NHC_2H_4SCH_3$ | $C_3H_7n$ | $C_2H_5$ | | m.p. 61–67° |
| 2.85 | $NHC_2H_4SCH_3$ | $C_3H_7n$ | $CH_2CH=CH_2$ | | |
| 2.86 | $NHC_2H_4SCH_3$ | $C_3H_7n$ | $CH_2CH=CHCl$ | | |
| 2.87 | $N(CH_3)_2$ | cyclopropyl | $CH_2CH=CH_2$ | | |
| 2.88 | $N(CH_3)_2$ | $C_3H_7n$ | $CH_2CH=CH_2$ | | oil |
| 2.89 | $N(CH_3)_2$ | $C_3H_7n$ | $C_4H_9n$ | | m.p. 67–70° |
| 2.90 | $N(CH_3)_2$ | $C_3H_7n$ | $C_6H_{13}n$ | | m.p. 65–68° |

TABLE 2-continued

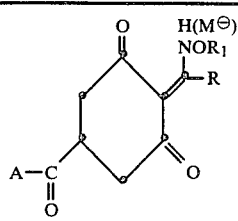

| No. | A | R | $R_1$ | $M^{\oplus}$ | Physical data |
|---|---|---|---|---|---|
| 2.91 | $N(CH_3)_2$ | $C_2H_5$ | $C_2H_5$ | | |
| 2.92 | $N(CH_3)_2$ | $C_2H_5$ | $CH_2CH=CH_2$ | | m.p. 82-83° |
| 2.93 | $N(CH_3)_2$ | $C_6H_{13}n$ | $C_2H_5$ | | |
| 2.94 | $N(CH_3)_2$ | $C_5H_{11}n$ | $CH_2CH=CH_2$ | | m.p. 64-66° |
| 2.95 | pyrrolidinyl | $C_3H_7n$ | $C_2H_5$ | | m.p. 77-85° (wax) |
| 2.96 | pyrrolidinyl | $C_8H_7n$ | | | |
| 2.97 | pyrrolidinyl | $C_3H_7n$ | $CH_2CH=CHCl$ | | |
| 2.98 | $NHCH_3$ | $C_3H_7n$ | $C_2H_5$ | | |
| 2.99 | $NHCH_3$ | $C_3H_7n$ | $CH_2CH=CH_2$ | | |
| 2.100 | $NHCH_3$ | $C_3H_7n$ | $CH_3$ | | m.p. 139-141 |
| 2.101 | $N(CH_3)$-phenyl | $C_3H_7n$ | $CH_2CH=CH_2$ | | m.p. 52-56° |
| 2.102 | $N(CH_3)$-phenyl | $C_3H_7n$ | $C_2H_5$ | | m.p. 93-95° |
| 2.103 | $N(CH_2CH=CH_2)_2$ | $C_3H_7n$ | $C_2H_5$ | | |
| 2.104 | $N(CH_2CH=CH_2)_2$ | $C_3H_7n$ | $CH_2CH=CH_2$ | | oil |
| 2.105 | $N(CH_2CH=CH_2)_2$ | $C_3H_7n$ | $CH_2CH=CHCl$ | | oil |
| 2.106 | $N(CH_2CH=CH_2)_2$ | $C_3H_7n$ | $CH_3$ | | |
| 2.107 | $NHCH_3$ | $C_3H_7n$ | $C_6H_{13}n$ | | |
| 2.108 | $NHCH_3$ | $C_3H_7n$ | $C_4H_9n$ | | |
| 2.109 | $NHCH_3$ | $C_5H_{11}n$ | $CH_2CH=CH_2$ | | |
| 2.110 | $NHCH_2$ | $C_6H_{13}n$ | $C_4H_9n$ | | |
| 2.111 | $NHC_2H_4SCH_3$ | $C_2H_5$ | $CH_2CH=CH_2$ | | |
| 2.112 | $NHC_2H_4SC_3H_7i$ | $C_3H_7n$ | $CH_2CH=CH_2$ | | |
| 2.113 | $NHC_2H_4SC_3H_7i$ | $C_3H_7n$ | $C_4H_9n$ | | |
| 2.114 | $N(CH_3)C_2H_5$ | $C_3H_7n$ | $CH_2CH=CH_2$ | | |
| 2.115 | $N(CH_3)C_2H_5$ | $C_3H_7n$ | $C_4H_9n$ | | |
| 2.116 | $N(CH_3)C_2H_5$ | $C_3H_7n$ | $CH_2CH=CH_2Cl$ | | |
| 2.117 | $N(CH_3)_2$ | $C_5H_{11}n$ | $C_2H_5$ | | |

In Examples 1a, 3a, 4a and 4b there are prepared novel intermediate products. According to these examples the following compounds are prepared

TABLE 3

| No. | A | $R_2$ | physical data |
|---|---|---|---|

| | | | | |
|---|---|---|---|---|
| 3.01 | N(CH$_3$)$_2$ | CH$_3$ | oil | |
| 3.02 | N(CH$_3$)$_2$ | H | m.p. 152–155° | |
| 3.03 | benzyloxy | H | | |
| 3.04 | 4-chlorobenzyloxy | H | | |
| 3.05 | CH$_3$OC$_2$H$_4$O | H | | |
| 3.06 | benzylamino | H | | |
| 3.07 | anilino | H | | |
| 3.08 | anilino | CH$_3$ | | |
| 3.09 | (CH$_3$)$_2$CHCH$_2$O | CH$_3$ | oil | |
| 3.10 | (CH$_3$)$_2$CHCH$_2$NH | H | | |
| 3.11 | (C$_2$H$_5$)$_2$N | H | oil | |
| 3.12 | 1-methylanilino | CH$_3$ | | |
| 3.13 | 1-methylanilino | H | m.p. 143–145 | |
| 3.14 | (CH$_2$=CHCH$_2$)$_2$N | CH$_3$ | oil | |
| 3.15 | (CH$_2$=CHCH$_2$)$_2$N | H | resin | |
| 3.16 | piperidino | CH$_3$ | | |
| 3.17 | piperidino | H | | |
| 3.18 | CH$_3$SC$_2$H$_4$NH | CH$_3$ | | |
| 3.19 | CH$_3$SC$_2$H$_4$NH | H | resin | |
| 3.20 | HSC$_2$H$_4$NH | CH$_3$ | wax | |
| 3.21 | HSC$_2$H$_4$NH | H | | |
| 3.22 | H$_5$C$_3$(CH$_3$)CHO | H | m.p. 76–78° | |

EXAMPLE 5

Formulation Examples for compounds of the formula I or mixtures thereof with herbicides

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphahalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thorougly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

EXAMPLE 6

Preemergence herbicidal activity

Plant seeds are sown in flower pots (diameter 11 cm) in a greenhouse. Immediately afterwards the surface of the soil is treated with an aqueous emulsion of the test compound at a concentration of 4 kg a.i. per hectare. The pots are then kept in the greenhouse at a temperature of 22°–25° C. and 50 to 70% relative humidity. The test is evaluated 3 weeks later and assessment of the action on the test plants is made in accordance with the following rating:

1: plant has not germinated or has totally withered
2–3: very pronounced action
4–6: medium action
7–8: poor action
9: no action (as untreated controls)

The results are as follows:

| Compound | Plant: Avena sativa | Setaria italica | Sinapis alba | Stellaria media |
|---|---|---|---|---|
| 2.37 | 1 | 1 | 9 | 9 |
| 2.47 | 1 | 1 | 9 | 9 |
| 2.61 | 1 | 1 | 9 | 9 |
| 2.63 | 3 | 1 | 9 | 9 |
| 2.64 | 1 | 2 | 8 | 8 |

EXAMPLE 7

Preemergence herbicidal activity

Different cultivated plants and weeds are reared from seeds in pots in a greenhouse until they have reached the 4- to 6-leaf stage. The plants are sprayed with an aqueous emulsion of test compound (prepared from a 25% emulsifiable concentrate) at a concentration of 4 kg/ha. The treated plants are then kept under optimum conditions of light, regular watering, temperature (22°–25° C.), and relative humidity (50–70%). The test is evaluated 15 days after treatment in accordance with the same rating as in Example 6.

The results are as follows:

| Compound | Plant: Avena sativa | Setaria italica | Lolium perenne | Solanum lycopersicum | Sinapis alba | Stellaria media | Phaseolus vulgaris |
|---|---|---|---|---|---|---|---|
| 2.37 | 1 | 2 | 2 | 9 | 8 | 8 | 7 |
| 2.47 | 2 | 4 | 2 | 4 | 6 | 8 | 9 |
| 2.61 | 1 | 2 | 2 | 7 | 7 | 8 | 9 |
| 2.63 | 1 | 1 | 2 | 8 | 5 | 8 | 5 |
| 2.64 | 1 | 1 | 2 | 4 | 7 | 8 | 9 |

EXAMPLE 8

Growth inhibition of tropical cover crops

The test plants (centrosema plumieri and centrosema pubescens) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

EXAMPLE 9

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of the formula I until thoroughly wetted. The rate of application corresponds to 100 g a.i. per hectare. Evaluation is made about 5 weeks after application. Compared with untreated controls, the compounds of the formula I markedly increase the number and weight of the harvested siliques on the leading shoot.

EXAMPLE 10

Growth inhibition of cereals

Summar barley (Hordeum vulgare) and summer rye (Secale) are sown in sterilised soil in plastic beakers in a greenhouse and watered as required. The cereal shoots are treated about 21 days after sowing with an aqueous spray mixture of a compound of the formula I. The concetration corresponds to 100 g of active ingredient per hectare. Evaluation of the growth of the cereals is made 21 days after application. A comparison with untreated controls shows that the growth of cereal plants treated with compounds of the formula I is significantly reduced (60–90% of the controls) and that the diameter of the stalks has in some cases increased.

EXAMPLE 11

Growth inhibition of grasses

Seeds of the grasses Lolium perenne, Poa pratensis, Festuca ovina, Dactylis glomerate and Cynodon dactylon are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of the formula I. The concentration of test compound corresponds to a rate of application of up to 100 g a.i. per hectare. The growth of the grasses is evaluated 21 days after application. The compounds of formula I effect a reduction in new growth in the range of 10–30% in comparison with untreated controls.

What is claimed is:

1. A cyclohexanedionecarboxylic acid derivative of the formula

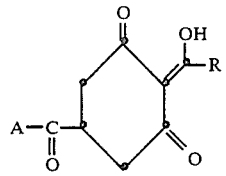

wherein A is an —NR$_3$R$_4$ radical, R is C$_1$–C$_6$alkyl which is unsubstituted or substituted by halogen, C$_1$–C$_6$alkoxy or C$_2$–C$_4$alkylthio, R$_3$ and R$_4$ are each independently hydrogen, C$_1$–C$_6$alkyl, C$_2$–C$_{10}$alkoxyalkyl, C$_2$–C$_{10}$alkylthioalkyl; C$_3$–C$_6$alkenyl, C$_3$–C$_6$alkynyl; one of R$_3$ and R$_4$ is also phenyl or benzyl, wherein the phenyl nucleus is unsubstituted or substituted by halogen, C$_1$–C$_4$alkyl, C$_1$–C$_4$alkoxy, C$_1$–C$_4$haloalkyl, nitro or cyano, or R$_3$ and R$_4$, together with the nitrogen atom to which they are attached form a pyrrolidine, piperidine or morpholine ring; or a metal or ammonium salt thereof.

2. N,N-dimethyl 4-(1-hydroxypropylidene)-3,5-cyclohexanedione carboxamide according to claim 1.

3. N-isobutyl 4-(1-hydroxybutylidene)-3,5-cyclohexanedione carboxamide according to claim 1.

4. A herbicidal and plant growth regulating composition, which contains at least one cyclohexandionecarboxylic acid derivative according to claim 1, together with carriers and/or other formulation assistants.

5. A method of selectively controlling weeds pre- or postemergence in crops of useful plants, which comprises applying to said useful plants or to the locus thereof an effective amount of a cyclohexanedionecarboxylic acid derivative according to claim 1.

6. A method of selectively controlling grasses pre- or postemergence in crops of useful plants, which comprises applying to said plants or to the locus thereof an effective amount of a cyclohexanedionecarboxylic acid derivative according to claim 1.

7. A method according to claim 6, wherein the crops of useful plants are sugar cane, cereals, maize, soya beans, rice and cotton.

8. A method of regulating plant growth, which comprises treating plants, parts of plants or seeds with an effective amount of a cyclohexanedionecarboxylic acid derivative according to claim 1.

9. A method of inhibiting plant growth preemergence beyond the 2-leaf stage, which comprises applying to said plants an effective amount of a cyclohexanedionecarboxylic acid derivative according to claim 1.

10. A method according to claim 9, wherein the plants are cover crops.

11. A method of regulating plant growth to obtain an increase in yield, which comprises applying to plants an effective amount of a cyclohexanedionecarboxylic acid derivative (according) to claim 1.

12. A method according to claim 11, wherein the plants are soya bean plants.

13. A method of controlling undesirable plant growth, which comprises applying an effective amount of a cyclohexanedionecarboxylic acid derivative according to claim 1 to the plant or the locus thereof.

14. A method of regulating plant growth, which comprises applying an effective amount of a cyclohexanedionecarboxylic acid derivative according to claim 1 to the plant or the locus thereof.

15. A method of inhibiting the growth of grasses, which comprises applying an effective amount of a cyclohexanedionecarboxylic acid derivative according to claim 1 to the plant or the locus thereof.

16. N-methoxy-N-methyl 4-(1-hydroxybutylidene)-3,5-cyclohexanedione carboxamide.

17. N-cyclopropyl-4-(1-hydroxybutylidene)-3,5-cyclohexanedione carboxamide.

* * * * *